United States Patent [19]
Leopoldi et al.

[11] 4,142,651
[45] Mar. 6, 1979

[54] FLUID DISPENSER WITH FLEXIBLE OUTLET TUBE AND PINCHING VALVE

[76] Inventors: Norbert Leopoldi, 4180 Marine Dr., Chicago, Ill. 60613; Leland K. Girard, 693 Madelyn Dr., Des Plaines, Ill. 60016

[21] Appl. No.: 792,319

[22] Filed: Apr. 29, 1977

[51] Int. Cl.² .................... B67D 3/00; F16K 7/06
[52] U.S. Cl. .................... 222/185; 222/507; 222/529; 251/7
[58] Field of Search ......... 222/527, 528, 529, 530, 222/537, 181, 185, 507, 514, 587, 205, 207, 425, 449; 251/7

[56] References Cited

U.S. PATENT DOCUMENTS

| | | | |
|---|---|---|---|
| 589,806 | 9/1897 | Bard | 251/7 X |
| 2,002,092 | 5/1935 | Juster | 222/587 |
| 2,963,205 | 12/1960 | Beall | 222/514 X |
| 3,305,144 | 2/1967 | Beres et al. | 222/529 X |
| 3,390,860 | 7/1968 | Kavanau | 222/529 X |
| 3,998,364 | 12/1976 | Hollander | 251/7 X |

Primary Examiner—Robert B. Reeves
Assistant Examiner—Francis J. Bartuska
Attorney, Agent, or Firm—McWilliams, Mann & Zummer

[57] ABSTRACT

A fluid dispenser including a container, or alternatively, one which is adapted to receive a bottle or the like for storing a supply of fluid, a push button valve, and a flexible tube connecting the container to the push button valve. The fluid flows by gravity from the container, through the flexible tubing, to the push button valve. The push button valve is spring-loaded, and has a pair of aligned openings through which the flexible tubing extends. In the inoperative or normal position of the push button valve, the flexible tubing is pinned shut at the point where it extends through the openings, thus cutting off the flow of fluid from the container to the push button valve. To operate the fluid dispenser, the push button valve is simply pressed downwardly to align the pair of openings, which reaction releases the crimping or pinching of the flexible tubing, allowing the fluid to flow through the flexible tubing.

6 Claims, 7 Drawing Figures

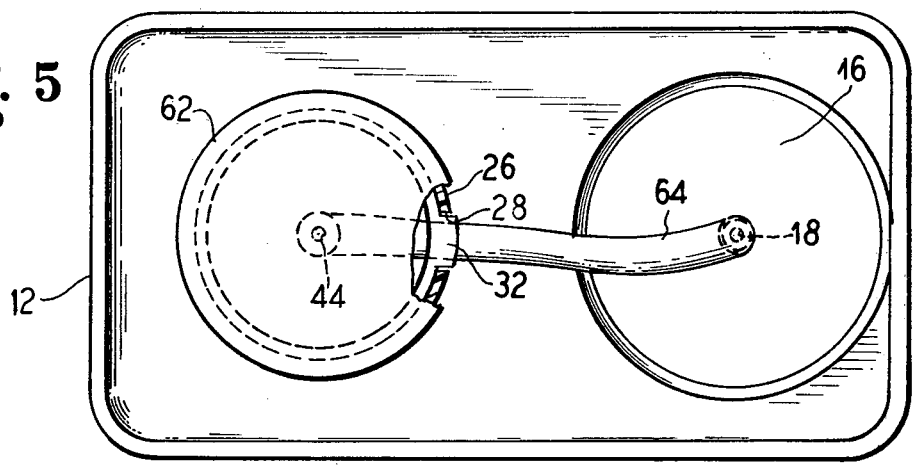
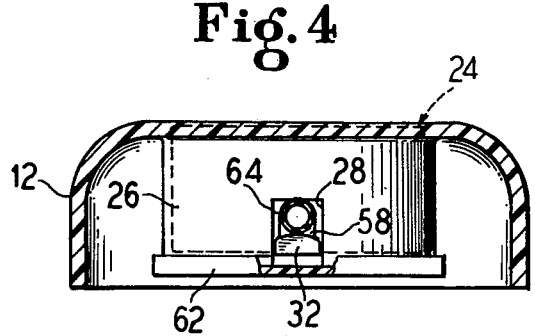
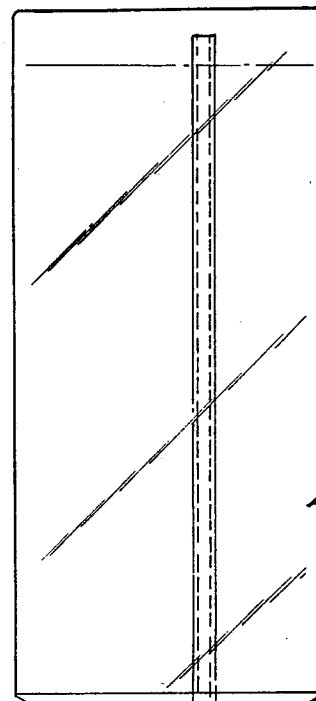
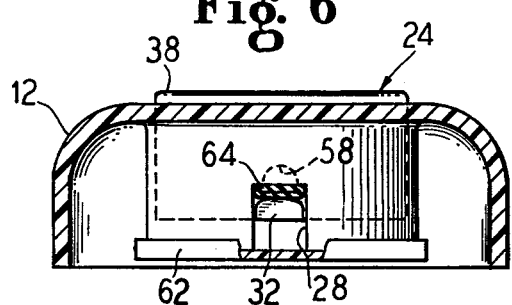
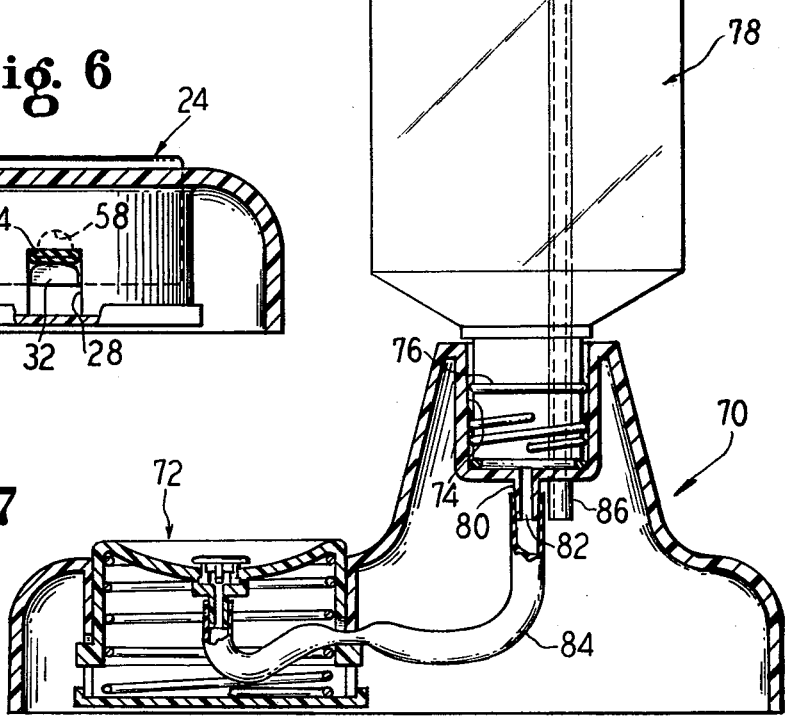

FLUID DISPENSER WITH FLEXIBLE OUTLET TUBE AND PINCHING VALVE

BACKGROUND OF THE INVENTION

This invention relates to improved fluid dispensers.

The improved fluid dispensers of the present invention find particular application in the pharmaceutical or medical field for dispensing fluids such as alcohol. Generally, presently available alcohol or fluid dispensers require a pumping action and normally the pump must be actuated four or five times by pressing and releasing the pump until the alcohol or fluid flows up into and through a dispensing orifice. Such alcohol dispensers are used by doctors for wetting a cotton swab preparatory to cleansing a spot or area on a patient's body. While these fluid dispensers are generally satisfactory, they have been found to be objectionable in that they have to be pumped numerous times in order to dispense the fluid and further that the pumping operation requires a two-handed operation.

BRIEF SUMMARY OF THE PRESENT INVENTION

In contrast to the above-described presently available fluid dispensers, the fluid dispenser of the present invention can be easily operated with one hand and fluid is dispensed immediately with the first operation or actuation of the dispenser's pushbutton.

More particularly, the fluid dispenser includes a container, or alternatively, is adapted to receive a bottle or the like, for storing a supply of the fluid; a pushbutton valve; and a flexible tube connecting the container to the pushbutton valve. The fluid flows by gravity from the container, through the flexible tubing to the pushbutton valve. The pushbutton valve is spring-loaded, and has a pair of aligned openings through which the flexible tubing extends. In the inoperative or normal position of the pushbutton valve, the flexible tubing is pinched shut at the point where it extends through the openings, thus cutting off the flow of fluid from the container to the pushbutton valve. To operate the fluid dispenser, the pushbutton valve is simply pressed downwardly to align the pair of openings, which action releases the crimping or pinching of the flexible tubing, allowing the fluid to flow through the flexible tubing.

The top wall of the pushbutton valve preferably and advantageously is dish-shaped, and a dispensing orifice is provided at its center such that the fluid can flow into the dish-shaped top wall. A cap or button preferably is provided over the dispensing orifice to permit the free flow of fluid from the orifice and to prevent the dispensing orifice from becoming clogged with cotton from cotton swabs which are wetted. In operation, the cotton swab is placed over the cap and the pushbutton valve actuated by pressing down on the cap. The fluid flows into the dish-shaped top wall from beneath and around the cap to wet the cotton swab.

Accordingly, it is an object of the present invention to provide improved fluid dispensers which do not require a pumping action and which are operable to dispense a fluid immediately upon being actuated.

BRIEF DESCRIPTION OF THE DRAWINGS

FIG. 4 is a sectional view taken along lines 4—4 of FIG. 3;

FIG. 5 is a bottom plan view, partially sectionalized, of the fluid dispenser of FIG. 1;

FIG. 6 is a sectional view taken along lines 6—6 of FIG. 2; and

FIG. 7 is a sectional view of a fluid dispenser exemplary of a second embodiment of the invention.

DETAIL DESCRIPTION OF THE INVENTION

Figure 1:
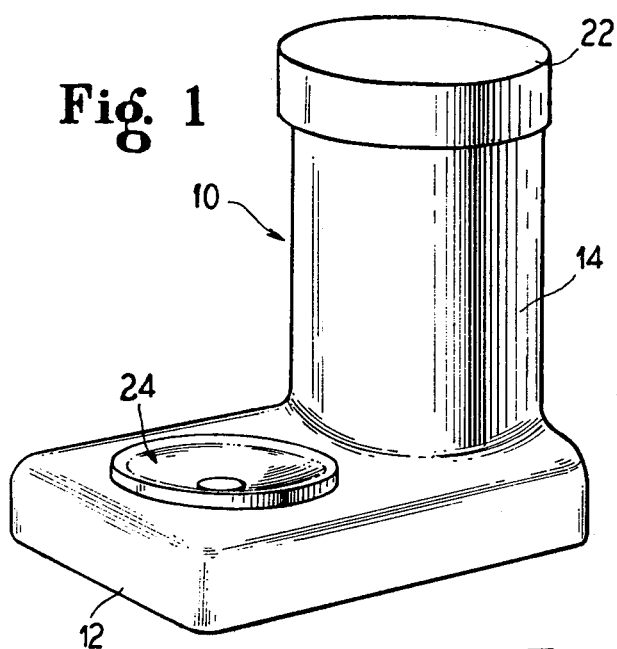
FIG. 1 is a perspective view of a fluid dispenser exemplary of a first embodiment of the invention.
Figure 2:
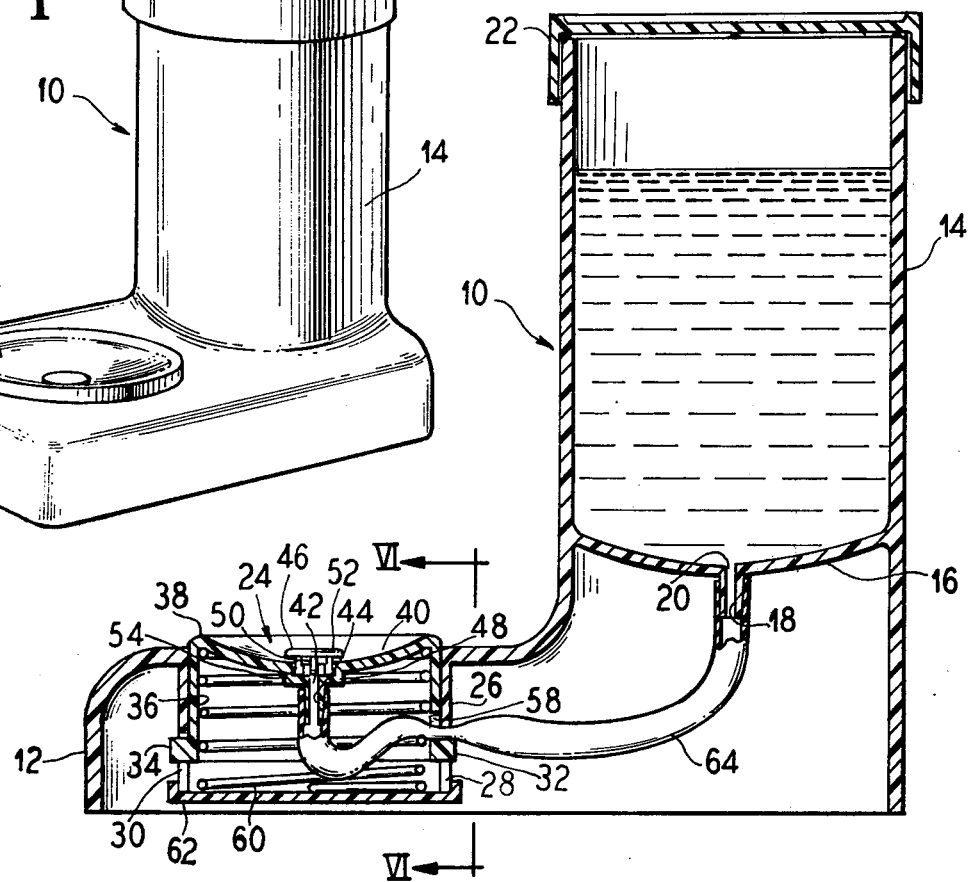
FIG. 2 is a sectional view of the fluid dispenser of FIG. 1, with the pushbutton valve thereof being in its normal position.

Referring now to the drawings, in FIG. 1 there is illustrated a fluid dispenser 10 exemplary of a first embodiment of the invention. The fluid dispenser 10, as can be best seen in FIGS. 1 and 2, generally has a base portion 12 which extends horizontally and a container portion 14 for fluids which is vertically disposed and is positioned at one end of the base portion 12. The base portion 12 and the container portion 14 preferably and advantageously are formed as an integral unit, by molding the same of a rigid plastic. In forming this integral unit, a bottom wall 16 is integrally formed therein for containing the fluid within the container portion 14. The bottom wall 16 also is formed with a cylindrical-shaped projection 18 which extends downwardly and has an orifice 20 therethrough for dispensing fluids from the container portion 14. The container portion 14 further is provided with a cover 22.

A pushbutton valve 24 is provided in the base portion 12. This pushbutton valve 24 is formed by a cylindrical-shaped side wall 26 which is integrally formed with the base portion 12 and forms a cavity which extends down into the base portion 12, as can be best seen in FIGS. 2 and 3. At least two elongated slots such as the slots 28 and 30 are formed in the side wall 26 for receiving therein locking lugs 32 and 34 formed on the side wall 36 of the pushbutton 38 of the pushbutton valve 24, for receiving the pushbutton 38 within the cavity or side wall 26.

The pushbutton 38 is hollow and has a side wall 36 which is cylindrical-shaped and proportioned to fit snugly within the cylindrical cavity formed by the side wall 26, and a top wall 40 which is concave or dish-shaped. As indicated above, locking lugs 32 and 34 are provided on the side wall 36 and engage within the elongated slots 28 and 30 in the side wall 26. The top wall 40 has a centrally disposed orifice 42 which extends into and through a cylindrical projection 44 integrally formed beneath the top wall 40.

A cap or button 46 preferably and advantageously is provided to prevent the orifice 42 from being clogged with cotton and to permit a free flow of fluid through the orifice 42 when the pushbutton valve 24 is actuated. This cap 46 is disposed within a well 48 formed in the top wall 40 in axial alignment with the orifice 42, and has legs 50 which support the top 52 thereof in a raised position so that fluid can flow through the orifice 42 into or onto the concave top wall 40. Locking tabs 54 are provided on the legs 50 and lockingly engage with the overhanging edge 56 of the top wall 40 to lockingly secure the cap 46 in the well 48.

An opening 58 is provided in the side wall 36 of the pushbutton 38 in alignment with one of the elongated slots, such as the elongated slot 28, as illustrated.

The pushbutton 38, and hence the pushbutton valve 24, normally is biased in an inoperative or normal position by means of a helical spring 60 which is disposed beneath the top wall 40 and confined therein by the side wall 36 and a retaining cover 62. The retaining cover 62 can be adhesively or otherwise secured to the side wall 36 at the terminal end thereof.

The fluid from the container 14 is coupled to the pushbutton valve 24 by means of a flexible tube 64 which has one end thereof friction-fitted to the projection 18 and its other end friction fitted to the projection 44. The flexible tube 64 is extended through the elongated slot 28 and through the opening 58 in the side wall 36 of the pushbutton 38. The fluid flows by gravity through the flexible tube 64, from the container 14 into the concave or dish-shaped top wall 40 of the pushbutton valve 24. In this respect, the bottom wall 16 of the container 14 is disposed so that the fluid level in the container 14 always is above the level of the top wall 40 of the pushbutton pump 24.

In assembling the fluid dispenser 10, the cap 46 is snap-fitted into the well 48, to lockingly engage the lugs 54 on the ends of its legs 50 within the overhanging edge 56 of the top wall 40. The pushbutton 38 is slidably inserted in the cavity formed by the side wall 26, by bowing the side wall 36 thereof inwardly so that the locking lugs 32 and 34 can pass into the cavity and lockingly engage within the respective elongated slots 28 and 30 in the side wall 26. The spring 60 is disposed within the cavity formed by the side wall 36 of the pushbutton 38. One end of the flexible tube 64 is fitted onto the projection 44 and its other end is extended through the spring 60, the opening 58 in the side wall 36 and the elongated slot 28 and fitted to the projection 18 at the bottom of the container 14. The spring 60 is secured within the cavity formed by the side wall 36, by securing the cover 62 to its terminal end. Fluid now can be disposed within the container 14, and the latter closed by means of the cover 22.

As indicated above, the spring 60 biases the pushbutton 38 upwardly, and in this position it is in its normal or inoperative position. In this normal position, the opening 58 in the side wall 36 of the pushbutton 38 is out of alignment with the elongated slot 28 in the side wall 26, so that the flexible tube 64 is crimped or pinched shut between the edges of the opening 58 and the elongated slot 28, as can be best seen in FIGS. 2 and 6. Accordingly, fluid is prevented from flowing through the flexible tube 64, from the container 14 into or onto the top wall 40 of the pushbutton 38.

Figure 3:
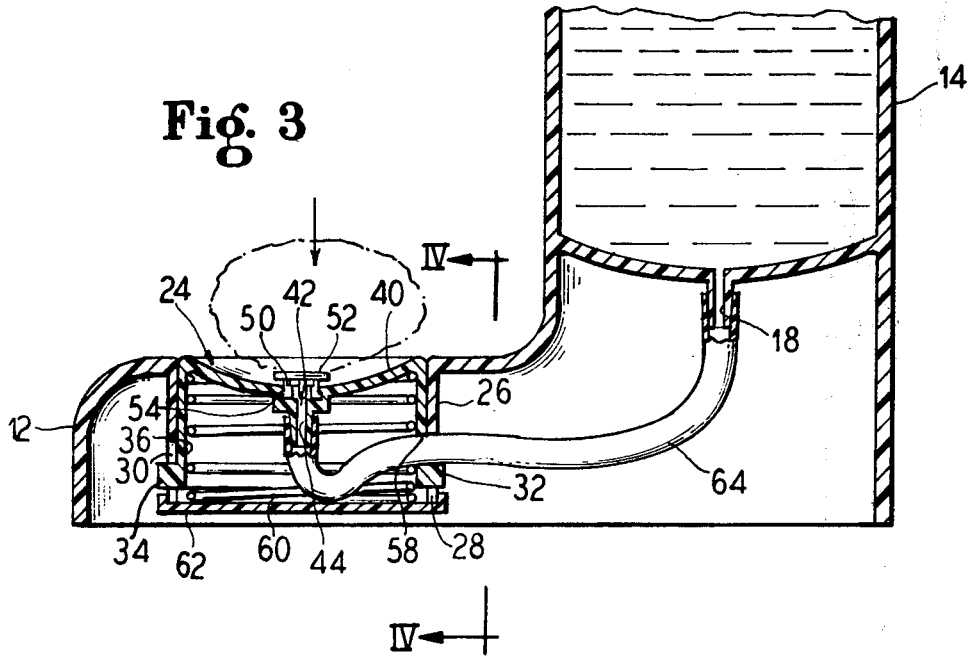
FIG. 3 is a partial sectional view like FIG. 2 illustrating the pushbutton valve in its actuated position.

In order to dispense some of the fluid, the pushbutton 38 simply is depressed until the opening 58 and the elongated slot 28 are aligned, so that the crimping or pinching of the flexible tube 64 is released, as can be best seen in FIGS. 3 and 4. Fluid now is permitted to flow by gravity from the container 14 through the flexible tube 64 into the dish-shaped top wall 40 of the pushbutton 38 of the pushbutton valve 24. The opening 58 and the elongated slot 28 therefor function as a simple and inexpensive shut-off valve for controlling the flow of fluid through the flexible tube 64. The pushbutton valve 24, furthermore, can be easily and simply operated with one hand, merely by depressing the pushbutton 38. When it is desired to wet a cotton swab or the like, the latter can be held between the fingers of one hand and pressed down on the cap 46 to depress the pushbutton 38, as illustrated in FIG. 3. The fluid flows from beneath the cap 46 in to the dish-shaped top wall 40, to wet the cotton swab.

In FIG. 7, there is illustrated another fluid dispenser 70 which has a pushbutton valve 72 that is of the same construction and operation as the pushbutton valve 24 of the fluid dispenser 10. The fluid dispenser 70, however, has a threaded cavity 74 for receiving therein the threaded neck portion 76 of the bottle 78 or the like. A projection 80 having an orifice 82 is formed on the bottom of the cavity 74, for receiving one end of the flexible tube 84 through which the fluid is conveyed to the pushbutton valve 72, as described above. An air tube 86 also is provided, and extends through the cavity 74 into the bottle 78 to admit air to the interior of the bottle.

The bottle 78 can be provided with the fluid dispenser 70 for filling with a fluid or, alternately, any bottle containing a fluid and having a properly proportioned neck portion can be simply affixed to the fluid dispenser 70.

From the above description, it can be seen that an improved fluid dispenser is provided which is easily operated to dispense a fluid with a one-handed operation. Furthermore, the fluid is immediately dispensed and without the necessity of having to pump the fluid dispenser several times, as in the past.

Now that the invention has been described, what is claimed as new and desired to be secured by Letters Patent is:

1. A fluid dispenser comprising: a base portion and a container portion integrally formed therewith; a pushbutton valve including a pushbutton which is slidably and reciprocally retained within a cavity formed in said base portion; said pushbutton and said cavity each having side walls, said side wall of said cavity having at least a pair of elongated slots formed in it and said side wall of said pushbutton having a pair of locking lugs formed on it which lockingly engage within said elongated slots to secure said pushbutton within said cavity; said pushbutton having a top wall which is concave and a projection beneath said top wall; said container portion having a bottom wall disposed at a level higher than said top wall of said pushbutton, a projection beneath said bottom wall and a flexible tube for conveying fluid by gravity flow from said container portion to said pushbutton coupled to said projection beneath said bottom wall of said container portion and said top wall of said pushbutton; an orifice extending through said projection beneath said top wall of said pushbutton, whereby a fluid is conveyed to the top wall of said pushbutton; said flexible tube extending through aligned openings in said side walls of said cavity and said pushbutton, said pushbutton being biased so that said openings are misaligned and the edges of said openings pinch said flexible tube closed to prevent fluid flow through said flexible tube, and being operable to substantially align said openings to release said flexible tube to permit fluid flow therethrough to the top wall of said pushbutton.

2. The fluid dispenser of claim 1, wherein one of said elongated slots forming said opening in said side wall of said cavity through which said flexible tube is extended.

3. The fluid dispenser of claim 1, further comprising spring means contained within said pushbutton and beneath said top wall thereof for biasing said pushbutton such that said opeings normally are misaligned.

4. The fluid dispenser of claim 1, further comprising a cap disposed over and above said orifice in said top wall of said pushbutton, whereby a free flow of fluid onto said top wall is permitted, said cap further preventing said orifice from becoming clogged.

5. The fluid dispenser of claim 1, wherein said container portion comprises a threaded cavity for threadedly receiving therein the threaded neck portion of a container, whereby a container for fluids can be secured to said fluid dispenser, said threaded cavity having a bottom wall which is disposed at a level higher than said top wall of said pushbutton whereby fluid flows by gravity through said flexible tube to said top wall of said pushbutton, tube attachment means having an orifice therethrough secured to said bottom wall of said threaded cavity, said one end of said flexible tube being attached to said tube attachment means.

6. The fluid dispenser of claim 5, further comprising an air tube extending through said bottom wall of said threaded cavity, said air tube extending into a container affixed within said threaded cavity to introduce air into said container.

* * * * *